US005206344A

United States Patent [19]

Katre et al.

[11] Patent Number: 5,206,344

[45] Date of Patent: Apr. 27, 1993

[54] INTERLEUKIN-2 MUTEINS AND POLYMER CONJUGATION THEREOF

[75] Inventors: Nandini Katre, El Cerrito; Robert F. Halenbeck, San Rafael; Robert J. Goodson, Albany; Peter C. McCabe, Pittsburg; Michael J. Knauf, San Bruno, all of Calif.

[73] Assignee: Cetus Oncology Corporation, Emeryville, Calif.

[21] Appl. No.: 142,467

[22] Filed: Jan. 11, 1988

Related U.S. Application Data

[63] Continuation-in-part of Ser. No. 866,459, May 21, 1986, abandoned, which is a continuation-in-part of Ser. No. 749,955, Jun. 26, 1985, abandoned.

[51] Int. Cl.[5] ...................... C07K 13/00; A61K 37/02

[52] U.S. Cl. .................................... 530/351; 530/402; 530/403; 530/404; 424/85.1; 424/85.2; 424/85.91; 930/141; 435/69.5; 435/69.52

[58] Field of Search .................. 424/85.1, 85.2, 85.91; 530/351, 402–404; 435/69.5, 69.52; 930/141

[56] References Cited

U.S. PATENT DOCUMENTS

| | | | |
|---|---|---|---|
| 3,619,371 | 6/1968 | Crook et al. | 424/88 |
| 3,788,948 | 1/1974 | Kagedal et al. | 435/180 |
| 3,876,501 | 4/1975 | Hanushewsky | 435/178 |
| 3,960,635 | 6/1976 | La Roy et al. | 156/286 |
| 3,960,830 | 6/1976 | Bayer et al. | 530/334 |
| 4,002,531 | 1/1977 | Royer | 435/188 |
| 4,055,635 | 10/1977 | Green et al. | 424/78 |
| 4,088,538 | 5/1978 | Schneider | 435/94 |
| 4,179,337 | 12/1979 | Davis et al. | 435/180 |
| 4,261,973 | 4/1981 | Lee et al. | 424/89 |
| 4,301,144 | 10/1981 | Iwashita et al. | 530/387 |
| 4,415,665 | 11/1983 | Mosbach et al. | 435/180 |
| 4,496,689 | 1/1985 | Mitra | 435/180 |
| 4,609,546 | 9/1986 | Hiratani | 514/2 |

FOREIGN PATENT DOCUMENTS

| | | |
|---|---|---|
| 152847 | 8/1985 | European Pat. Off. . |
| 154316 | 9/1985 | European Pat. Off. . |
| 1198699 | 1/1986 | Japan . |
| 8604145 | 7/1986 | PCT Int'l Appl. . |
| 8700056 | 1/1987 | PCT Int'l Appl. . |

OTHER PUBLICATIONS

Regenmorfel, *TIBS* 11, Jan. 1986, pp. 36–39.
Cohen et al., *Science,* 234, 1986, pp. 349–351.
Brandhuber et al., *Science,* 238, 1987, pp. 1707–1709.
Ju et al., *J. Biol. Chem.,* 262, 1987, pp. 5723–5731.
Savoca et al., *Biochemica Biophysica Acta,* 578, 1979, pp. 47–53.
Abuchowski et al., *JBC* 252, 1977, pp. 3578–3581.
Boccu et al., *Z. Naturforsch* 38, 1983, pp. 94–99.
King et al., *Inst. Arch. Allergy Appl. Immun.* 66, 1981, pp. 439–446.
U. K. et al. *Int. Arch Allergy Appl. Immun.* 74, 1984, pp. 55–62.
Inada et al., *Biochem and Biophys. Res. Comm.,* 122:845–850 (1984).
Takahashi et al., *Biochem. and Biophys. Res. Comm.,* 121:261–265 (1984).
Suzuki et al., *Biochem. Biophys. Acta.,* 788:248–255 (1984).
Abuchowski et al., *Cancer Biochem. Biophys.,* 7:175–186 (1984).
Davis et al., *Biomedical Polymers,* (New York: Academic Press):441–451 (1980).

*Primary Examiner*—Garnette D. Draper
*Attorney, Agent, or Firm*—Philip L. McGarrigle; Janet E. Hasak

[57] ABSTRACT

Muteins of IL-2 in which one of the amino acids of the mature native sequence of IL-2 is replaced by a cysteine residue are prepared and conjugated through the replaced cysteine residue to a polymer selected from polyethylene glycol homopolymers or polyoxyethylated polyols, wherein said homopolymers are unsubstituted or substituted at one end with an alkyl group. These muteins are made via host expression of mutant genes encoding the muteins that have been changed from the genes for the parent proteins by site-directed mutagenesis. In addition, other species of IL-2 may be conjugated via the cysteine residue at position 125 of the mature IL-2 protein that is not necessary for the biological activity of the IL-2.

12 Claims, No Drawings

INTERLEUKIN-2 MUTEINS AND POLYMER CONJUGATION THEREOF

This application is a continuation-in-part application of copending U.S. application Ser. No. 866,459 filed May 21, 1986 now abandoned which is a continuation-in-part of U.S. application Ser. No. 749,955 filed Jun. 26, 1985, now abandoned.

BACKGROUND OF THE INVENTION

This invention relates to a chemical modification of biologically active interleukin-2 (IL-2) that alters the chemical and/or physiological properties of the IL-2 and an IL-2 mutein specifically designed for that purpose. More specifically, this invention relates to selective conjugation of IL-2 through its cysteine residues to polymers and to mutationally altered biologically active IL-2 muteins that differ from their parent analogs by the substitution of a particular amino acid with cysteine.

The use of polypeptides in circulatory systems for the purpose of producing a particular physiological response is well known in the medicinal arts. A limitation to the potential therapeutic benefit derived from the clinical use of polypeptides is their ability to elicit an immune response in the circulatory system. This immune response may be caused by aggregates in the material prior to injection as described by R. Illig (1970), *J. Clin. Endrocr.*, 31, 679–688, W. Moore (1978), *J. Clin. Endrocrinol. Metab.*, 46, 20–27 and W. Moore and P. Leppert (1980), *J. Clin. Endrocrinol. Metab.*, 51, 691–697. This response involves the production of antibodies to the polypeptides by the circulatory system into which they are injected. This antibody production may decrease or eliminate the desired biological function of the polypeptide, sometimes by causing reduced residence time in the circulatory system (reduced half-life) or by modifying the molecule by virtue of the antibody-polypeptide interaction.

Modification of these potentially useful therapeutic polypeptides so as to preclude or at least reduce an immune response while still maintaining desired physiological activities of the polypeptide would allow the use of these polypeptides in the mammalian circulatory system without the aforementioned disadvantages. In addition, due to the increased half-life of the circulating polypeptide, smaller amounts of the polypeptide would be required for the desired therapeutic effect than have heretofore been possible.

The problems of immunogenicity and short half-life in circulation set forth hereinabove and other undesirable properties of certain proteins are well recognized and various methods have been undertaken to solve them. One includes the modification of proteins with substantially straight-chain polymers such as polyethylene glycol (PEG) or polypropylene glycol (PPG). For example, U.S. Pat. No. 4,261,973 describes conjugation of immunogenic allergen molecules with non-immunogenic water-soluble polymers such as PEG to reduce the immunogenicity of the allergen. U.S. Pat. No. 4,301,144 describes conjugation of hemoglobin to PEG, PPG, a copolymer of ethylene glycol with propylene glycol, or ethers, esters or dehydrated products of such polymers to increase the oxygen-carrying ability of the hemoglobin molecule. U.S. Pat. No. 4,609,546 discloses that conjugating of a polypeptide or glycoprotein to a polyoxyethylene-polyoxypropylene copolymer increases its physiological activity. Preferably the polypeptide or glycoprotein is an enzyme or native interferon, which are water soluble. U.S. Pat. No. 4,179,337 discloses conjugating of water-soluble polypeptides such as enzymes and insulin to PEG or PPG to reduce the immunogenicity of the polypeptide while retaining a substantial proportion of its desired physiological activity. U.S. Pat. No. 4,002,531 discloses a different method of conjugating enzymes to PEG through an aldehyde derivative.

U.S. Pat. No. 3,960,635 discloses pharmaceutical compositions comprising a water-soluble complex of a proteolytic enzyme linked covalently to a polymeric substance such as polysaccharides.

U.S. Pat. No. 3,960,830 discloses peptides bound to a polyalkylene glycol polymer such as polyethylene glycol.

U.S. Pat. No. 4,088,538 discloses a reversibly soluble enzymatically active polymer enzyme product comprising an enzyme covalently bonded to an organic polymer such as polyethylene glycol.

U.S. Pat. No. 4,415,665 discloses a method of conjugating an organic ligand containing at least one primary or secondary amino group, at least one thiol group and/or at least one aromatic hydroxy group (described in col. 3, lines 19–36) to a polymeric carrier with at least one hydroxyl group (described in col. 2, lines 42–66).

U.S. Pat. No. 4,496,689 discloses a covalently attached complex of alpha-1-proteinase inhibitor with a polymer such as PEG or methoxypolyethylene glycols.

U.S. Pat. No. 3,619,371 discloses a polymeric matrix having a biologically active substance chemically bound thereto.

U.S. Pat. No. 3,788,948 discloses use of organic cyanate compounds to bind proteins to polymers.

U.S. Pat. No. 3,876,501 discloses activation of water-soluble carbohydrates with cyanogen bromide to improve their binding to enzymes and other proteins.

U.S. Pat. No. 4,055,635 discloses pharmaceutical compositions of a proteolytic enzyme linked covalently to a polymeric substance.

EP 152,847 discloses an enzyme conjugate composition comprising an enzyme conjugate, a calcium salt, and a polyethylene glycol.

In addition to these patents and patent publications, several articles discuss the concept of using activated PEG or PPG as a modifying agent for proteins such as enzymes, IgG and albumin. For example, Inada et al., *Biochem and Biophys. Res. Comm.*, 122, 845–850 (1984) disclose modifying water-soluble lipoprotein lipase to make it soluble in organic solvents such as benzene by using cyanuric chloride to conjugate with PEG. Takahashi et al., *Biochem. and Biophys. Res. Comm.*, 121, 261–265 (1984) disclose modifying horseradish peroxidase using cyanuric chloride triazine with PEG to make the water-soluble enzyme active and soluble in benzene. Suzuki et al., *Biochem. Biophys. Acta*, 788, 248–255 (1984) disclose suppression of aggregation of IgG using cyanuric chloride activated PEG. Abuchowski et al., *Cancer Biochem. Biophys.*, 7, 175–186 (1984) state that modification of asparaginases from *E. coli* and *Vibrio succinogenes* using PEG activated by succinimidyl succinate increases the half-life and decreases the immunogenicity of the proteins. Davis et al., *Biomedical Polymers*, (New York: Academic Press, 1980), p. 441–451 disclose that enzymes normally insoluble may be solubilized by PEG attachment without further details. Several other articles discuss modification of enzymes such as uricase, streptokinase, catalase, arginase and asparaginase with PEG activated by succinimidyl succinate or cyanuric chloride to increase half-life and decrease the immunogenicity of the protein.

None of these references, however, disclose specific IL-2 muteins obtained by site-directed mutagenesis and designed for conjugation to the PEG via an added cysteine residue nor conjugation of any IL-2 to PEG via cysteine residues. (U.S. Pat. No. 4,518,584 issued May 21, 1985 discloses IL-2 muteins wherein the cysteines are replaced by serines.) Furthermore, it is not a priori possible to predict which selected proteins would be favorably responsive to treatment with polymers due to the vast difference in the pharmacokinetics and physical properties of various proteins. Furthermore, none of the references disclose reducing or eliminating aggregation of the protein, a phenomenon that elicits an immune response when the protein is introduced in vivo.

EP 154,316, published Sep. 11, 1985 to Takeda Chemical Industries, Ltd., discloses and claims chemically modified lymphokines such as IL-2 containing PEG bonded directly to at least one primary amino group of a lymphokine.

In addition, WO 86/04145, published Jul. 17, 1986 to University of New Mexico discloses covalent modification of proteins with PEG employing an active ester intermediate.

Finally, PCT W087/00056 published Jan. 15, 1987 (Cetus Corporation) discloses that IL-2, IFN-$\beta$ and immunotoxins may be conjugated to PEG or polyoxyethylated polyols by means of lysines or cysteines on the protein.

SUMMARY OF THE INVENTION

Accordingly, the present invention provides, in one aspect, for modifying interleukin-2 at one or more specific cysteine residues on the molecule to make a more homogeneous modified IL-2.

In addition, the modification may increase the physiological half-life of the IL-2 and decrease its immunogenicity by reducing or eliminating aggregation of the IL-2 or by masking antigenic determinants.

In one aspect, the present invention relates to a recombinant human interleukin-2 mutein wherein one of the non-cysteine amino acid residues of mature, native, human interleukin-2 is replaced by a cysteine residue and said mutein exhibits at least one of the useful in vitro or ex vivo biological activities associated with native, human interleukin-2. This inserted cysteine can then be covalently attached to a reactive group of a polymer as described below. Preferably, the threonine at position 3 is replaced with a cysteine residue.

The invention herein also encompasses a structural gene having a DNA sequence encoding the above mutein, an expression vector that includes this structural gene, for example, plasmid pC31L-2, a host cell or organism such as *E. coli* transformed with this expression vector, and progeny thereof.

The invention further relates to an oligonucleotide for use in oligonucleotide-directed mutagenesis for engineering a gene with a DNA sequence encoding the above mutein comprising a nucleotide sequence that is complementary to a region of the strand of the gene that includes the codon for the threonine residue or the antisense triplet paired with said codon, as the case may be, except for mismatches with said codon that define a triplet that codes for a cysteine residue.

In another embodiment, the invention is directed to a composition comprising an IL-2 or mutein thereof covalently conjugated (via one or more of those cysteine residues of the IL-2 that, if on the native IL-2, are not necessary for its biological activity) to a water-soluble polymer selected from the group consisting of polyethylene glycol homopolymers and polyoxyethylated polyols, wherein said homopolymer is unsubstituted or substituted at one end with an alkyl group (and said polyol is unsubstituted at both ends).

Preferably the polymer is unsubstituted polyethylene glycol (PEG), monomethyl PEG (mPEG), or polyoxyethylated glycerol (POG), and it is coupled to the protein via a thioether bond formed from a maleimido group on the polymer.

In yet another aspect, the present invention is directed to a pharmaceutical composition comprising a non-toxic, inert, pharmaceutically acceptable aqueous carrier medium in which is dissolved the biologically active selectively conjugated IL-2 or mutein thereof, wherein one or more cysteine residues of the IL-2 not necessary for the biological activity of the IL-2 are covalently conjugated to the water-soluble polymer identified above.

Another aspect of this invention resides in a process for preparing the conjugated IL-2 comprising:

(a) preparing a water-soluble polymer having at least one terminal reactive group where the polymer is selected from the group consisting of polyethylene glycol homopolymers and polyoxyethylated polyols, wherein said homopolymer is unsubstituted or substituted at one end with an alkyl group (and said polyol is unsubstituted at both ends); and (b) reacting the IL-2 or mutein thereof with the reactive group of said polymer so as to conjugate covalently the polymer to the IL-2 via one or more cysteine residues on the IL-2 or mutein that, if on the native IL-2, are not necessary for the biological activity of the IL-2.

A pharmaceutical composition can be prepared by the additional step of (c) formulating said conjugated protein in a non-toxic, inert, pharmaceutically acceptable aqueous carrier medium.

In a still further aspect, the invention encompasses a process for isolating and purifying an IL-2 mutein from yeast transformed with DNA encoding said mutein, comprising:

(a) culturing the transformed yeast;
(b) harvesting and centrifuging the cultured yeast and retaining the supernatant;
(c) adding a chelating agent to the supernatant and adjusting the pH of the supernatant to between about 4 and 5;
(d) concentrating the supernatant and adding a surfactant thereto;
(e) passing the supernatant through a molecular sizing column and isolating the fraction from the column with the highest IL-2 bioactivity;
(f) concentrating the fraction;
(g) passing the concentrated fraction through a reverse-phase high performance liquid chromatography column; and
(h) collecting the fraction with highest IL-2 bioactivity from the column.

DESCRIPTION OF THE PREFERRED EMBODIMENTS

"Recombinant host cells," "host cells,", "cells," "cell cultures," and so forth are used interchangeably, and designate individual cells, cell lines, cell cultures, and harvested cells that have been, or are intended to be, transformed with the recombinant vectors of this invention. These terms also include the progeny of the cells originally receiving the vector. It is well understood that not all of the progeny of a single cell are precisely, necessarily identical to the parent, due to spontaneous or intentional mutations or alterations in the culture conditions. These progeny are also included in the definition, so long as the capacity to perform the function of producing the mutein of the invention conferred by the vector is retained.

"Transformed" refers to any process for altering the DNA content of the host, including in vitro transformation procedures as described below, phage infection, or such other means for effecting controlled DNA uptake as are known in the art.

"Operably linked" as used herein regarding DNA sequences or genes refers to the situation wherein the sequences or genes are juxtaposed in such a manner as to permit their ordinary functionality. For example, a promoter operably linked to a coding sequence refers to those linkages where the promoter is capable of controlling the expression of the sequence.

The expression "control sequences" refers to DNA sequences that control the expression of the sequence that encodes the mutein herein. Examples include promoters for transcription initiation, optionally with an operator, enhancer regions, ribosome binding site sequences, and translation signals that initiate and terminate translation of the gene. Such control sequences must be compatible with, i.e., operable in, the host into which they will be inserted.

The term "muteins" refers to genetically engineered proteins expressed from a nucleic acid sequence that has been altered using techniques such as site-specific mutagenesis. Such genetic alterations are designed to result in one or more substitutions, additions, or deletions to the amino acid sequence of the parent protein.

Cysteine residue of native IL-2 "not necessary for its biological activity" refers to the cysteine residue at position 125, numbered in accordance with mature native IL-2.

"Useful in vitro or ex vivo biological activities associated with recombinant, human IL-2" refers to biological activities of interleukin-2 that are useful, such as those associated with tumor regression, viral inhibition, immunomodulating activity, lymphokine-activated lymphocyte activity, T cell growth, natural killer activity, and treatment of infections caused by primary immunodeficiencies as described in copending U.S. application Ser. No. 125,380 filed Nov. 25, 1987now abandoned, entitled "Treatment of Infections Caused by a Primary Immunodeficiency With Interleukin-2".

The interleukin-2 herein may be obtained from tissue cultures or by recombinant techniques, and from any mammalian source such as, e.g., mouse, rat, rabbit, primate, pig, and human. Preferably, the IL-2 is human IL-2, and more preferably is recombinant, human IL-2.

The term "recombinant interleukin-2, " designated as IL-2, preferably human IL-2, refers to interleukin-2, having comparable biological activity to native IL-2, prepared by recombinant DNA techniques as described, e.g., by Taniguchi et al., *Nature,* 302:305–310 (1983) and Devos, *Nucleic Acids Research,* 11:4307–4323 (1983). In general, the gene coding for IL-2 is excised from the genome and inserted into a cloning vector to be cloned and then into an expression vector, which is used to transform a host organism, preferably a microorganism, and most preferably *E. coli.* The host organism expresses the foreign gene to produce IL-2 under expression conditions.

The IL-2 employed herein, in one preferred embodiment, has the native sequence of IL-2, with the cysteine residue at position 125 of the native molecule reacted with the polymer.

In another preferred embodiment, the IL-2 is a mutein wherein one of the non-cysteine amino acids of the IL-2, e.g., between positions 1 and 20 (N-terminus), numbered in accordance with mature, native human IL-2 (i.e., IL-2 without the leader sequence), is replaced with a cysteine residue. More preferably, the threonine at position 3 of the mature, native-sequence IL-2 (not with a leader sequence) is replaced with a cysteine residue.

This replacement may be the only change from the native sequence or may be one of two or more replacements of amino acids. In the latter instance, the replacements may take place in any order. For example, one may first prepare the IL-2 mutein described in U.S. Pat. No. 4,518,584, in which the cysteine normally occurring at position 125 of the wild-type or native molecule has been replaced by a neutral amino acid such as serine or alanine. In addition, the N-terminal alanyl residue of the IL-2 may be deleted. The resulting IL-2 mutein, e.g., $ala_1ser_{125}$IL-2, $ala_1ala_{125}$IL-2, des-$ala_1ser_{125}$IL-2 or des-$ala_1ala_{125}$IL-2, may be used to construct the preferred IL-2 mutein wherein the threonine normally occurring at position 3 of the mature, native molecule is replaced by cysteine, e.g., $ala_1cys_3ser_{125}$IL-2, $ala_1cys_3ala_{125}$IL-2, des-$ala_1cys_3ser_{125}$IL-2 or des-$ala_1cys_3ala_{125}$IL-2, where "des-$ala_1$" indicates that the N-terminal alanine is removed.

Alternatively or conjunctively, the IL-2 mutein may be one as described in copending U.S. application Ser. No. 810,656 filed Dec. 17, 1985 now abandoned, the disclosure of which is incorporated herein by reference, in which the methionine normally occurring at position 104 of the wild-type or native molecule has been replaced by a neutral amino acid such as alanine. The resulting muteins, e.g., des-$ala_1ala_{104}$IL-2, des-$ala_1ala_{104}ser_{125}$IL-2, $ala_1ala_{104}$IL-2, $ala_1ala_{104}ala_{125}$IL-2, des-$ala_1ala_{104}ala_{125}$IL-2, or $ala_1ala_{104}ser_{125}$IL-2 may be used to construct the preferred IL-2 muteins with the threonine at position 3 of the native molecule replaced by cysteine, e.g., des-$ala_1cys_3ala_{104}$IL-2, des-$ala_1cys_3ala_{104}ser_{125}$IL-2, $ala_1cys_3ala_{104}$IL-2, $ala_1cys3ala_{104}ala_{125}$IL-2, des-$ala_1cys_3ala_{104}ala_{125}$IL-2, or $ala_1cys3ala_{104}ser_{125}$IL-2.

In summary, the IL-2 herein is preferably a protein produced by a microorganism that has been transformed with the human cDNA sequence of IL-2 that encodes a protein with an amino acid sequence at least substantially identical to the amino acid sequence of native human IL-2, and with the disulfide bond of the cysteines at positions 58 and 105, and has biological activity which is common to native human IL-2. Substantial identity of amino acid sequences means the sequences are identical or differ by one or more amino acid alterations (deletions, additions, substitutions) that do not cause an adverse functional dissimilarity between the synthetic/recombinant protein and native human IL-2. Examples of IL-2 proteins with such properties include those described by Taniguchi et al., supra; Devos, supra; European Patent Publication Nos. 91,539 and 88,195; U.S. Pat. 4,518,584, supra. and copending U.S. application Ser. No. 810,656 filed Dec. 17, 1985, supra. Most preferably, the IL-2 is native sequence IL-2, des-$ala_1$IL-2, des-$ala_1ala_{104}$IL-2, $cys_3ser_{125}$IL-2, des-$ala_1cys_3ser_{125}$IL-2, $cys_3$ala125IL-2, des-$ala_1cys_3ala_{125}$IL-2, $cys_3ala_{104}$IL-2, des-$ala_1cys_3ala_{104}$IL-2, $cys_3ala_{104}ser_{125}$IL-2, $cys_3ala_{104}ala_{125}$IL-2, des-$ala_1cys_3ala_{104}ala_{125}$IL-2, or des-$ala_1cys_3$ala104ser125IL-2.

The precise chemical structure of the IL-2 proteins herein will depend on a number of factors. As ionizable amino and carboxyl groups are present in the molecule, a particular IL-2 protein may be obtained as an acidic or basic salt, or in neutral form. All such preparations that retain their bioactivity when placed in suitable environmental conditions are included in the definition of proteins herein. Further, the primary amino acid sequence of the IL-2 protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of recombinant IL-2 herein so long as the bioactivity of the IL-2 protein is not rendered significantly less useful, typically at least about 20% of the specific activity of IL-2. It is expected, of course, that such modifications may quantitatively or qualitatively affect the bioactivity by either enhancing or diminishing the activity of the IL-2 protein in the various assays.

The $cys_3$IL-2 muteins are preferably prepared as follows: A DNA sequence encoding the native sequence or other reference mutein, cloned into a convenient M-13 cloning vector, is subjected to site-specific mutagenesis using the appropriate primer to convert the residue at position 3 from threonine to cysteine, as described below.

The resulting DNA is then ligated into expression vectors using standard procedures, which can be precisely identical to those used in preparing expression vectors for the starting sequence. The $cys_3$IL-2 mutein may then be produced in suitable hosts under the control of compatible control sequences using any of the recombinant host cell systems known in the art, described below. The threonine-replaced muteins thus produced are recovered and purified using standard protein purification techniques, described below.

Most of the techniques that are used to transform cells, construct vectors, effect hybridization with probe, and the like are widely practiced in the art, and most practitioners are familiar with the standard resource materials that describe specific conditions and procedures. However, for convenience, the following paragraphs may serve as a guideline.

The method herein for producing the recombinant IL-2, particularly $cys_3$IL-2, is not limited to the particular host or control sequence employed. Either procaryotic or eucaryotic hosts may be used for expression of DNA sequences; cloning of such sequences generally employs procaryotes for convenience. Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors that contain replication sites and control sequences derived from a species compatible with the host are used. For example, *E. coli* is typically transformed using derivatives of pBR322, a plasmid derived from an *E. coli* species by Bolivar, et al., *Gene* (1977) 2:95. pBR322 contains genes for ampicillin and tetracycline resistance, and thus provides additional markers that can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems, (Chang, et al., *Nature* (1977) 198:1058) and the tryptophan (trp) promoter system (Goeddel, et al., *Nucleic Acids Res.* (1980) 8:4057), and the lambda-derived $P_L$ promoter (Shimatake, et al., *Nature* (1981) 292:128) and N-gene ribosome binding site, which has been made useful as a portable control cassette, which comprises a first DNA sequence that is the $P_L$ promoter operably linked to a second DNA sequence corresponding to $N_{RBS}$ upstream of a third DNA sequence having at least one restriction site that permits cleavage within six bp 3' of the $N_{RBS}$ sequence. Also useful is the phosphatase A (phoA) system described by Chang et al. in Eur. Pat. Pub. No. 196,864 published Oct. 8, 1986. However, any available promoter system compatible with procaryotes can be used.

In addition to bacteria, eucaryotic microbes, such as yeast and Aspergillus, may also be used as hosts. Laboratory strains of *Saccharomyces cerevisiae*, Baker's yeast, are most used, although a number of other strains are commonly available. Plasmid vectors suitable for yeast expression include use of the 2 micron origin of replication (Broach, J. R., *Meth. Enz.* (1983) 101:307), and those described by, for example, Stinchcomb, et al., *Nature* (1979) 282:39, Tschempe, et al., *Gene* (1980) 10:157 and Clarke, L., et al., *Meth. Enz.* (1983) 101:300). Control sequences for yeast vectors include promoters for the synthesis of glycolytic enzymes (Hess, et al., *J. Adv. Enzyme Reg.* (1968) 7:149; Holland, et al., *Biochemistry* (1978) 17:4900).

Additional promoters known in the art include the promoter for 3-phosphoglycerate kinase (Hitzeman, et al., *J. Biol. Chem.* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization.

It is also believed that yeast terminator sequences are desirable at the 3' end of the coding region. Such terminators are found in the 3' untranslated region following the coding sequences in yeast-derived genes.

Many of the vectors illustrated contain control sequences derived from the enolase gene containing plasmid peno46 (Holland, M. J., et al., *J. Biol. Chem.* (1981) 256:1385) or the LEU2 gene obtained from YEp13 (Broach, J., et al., *Gene* (1978) 8:121); however, any vector containing a yeast-compatible promoter, origin of replication, and other control sequences is suitable.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas N51, VERO, and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al., *Nature* (1978) 273:113), or other viral promoters such as those derived from polyoma, Adenovirus 2, bovine papilloma virus, or avian sarcoma viruses, or immunoglobulin promoters and heat shock promoters. A system for expressing DNA in mammalian systems usng the BPV as a vector is disclosed in U.S. Pat. No. No. 4,419,446. A modification of this system is described in U.S. Pat. No. No. 4,601,978. General aspects of mammalian cell host system transformations have been described by Axel; U.S. Pat. No. No. 4,399,216 issued Aug. 16, 1983. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker, A., et al., *J. Mol. Appl. Gen.* (1982) 1:561) are available.

Recently, in addition, expression systems employing insect cells utilizing the control systems provided by baculovirus vectors have been described (Miller et al., in *Genetic Engineering* (1986) Setlow, J. K., et al., eds., Plenum Publishing, Vol. 8, pp.277-297). These systems are also successful in producing the $cys_3IL$-2 muteins herein.

Depending on the host cell used, transformation is done using standard techniques appropriate to such cells. The calcium treatment employing calcium chloride, as described by Cohen, S. N., *Proc. Natl. Acad. Sci. (USA)* (1972) 69:2110, is useful for procaryotes or other cells that contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bact.* (1977) 130:946 and Hsiao, C. L., et al., *Proc. Natl. Acad. Sci. (USA)* (1979) 76:3829. Transformation into insect cells may be accomplished using a baculovirus expression vector as described in EP 127,839, supra.

cDNA or genomic libraries may be probed in accordance with the procedure described by T. Maniatis et al., *Molecular Cloning-A Laboratory Manual* (Cold Spring Harbor Laboratories, 1982).

Construction of suitable vectors containing the desired coding and control sequences employs standard ligation and restriction techniques that are well understood in the art. Isolated plasmids, DNA sequences, or synthesized oligonucleotides are cleaved, tailored, and religated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See, e.g., New England Biolabs Product Catalog. In general, about 1 μg of plasmid or DNA sequence is cleaved by one unit of enzyme in about 20 μl of buffer solution; in the examples herein, typically, an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction-cleaved fragments may be blunt ended by treating with the large fragment of *E. coli* DNA polymerase I (Klenow) in the presence of the four deoxyribonucleoside triphosphates (dNTPs) using incubation times of about 15 to 25 minutes at 20° to 25° C. in 50 mM Tris pH 7.6, 50 mM NaCl, 6-10 mM $MgCl_2$, 6-10 mM DTT and 5-100 μM dNTPs. The Klenow fragment fills in at 5′ sticky ends, but chews back protruding 3′ single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared using the triester method of Matteucci, et al., (*J. Am. Chem. Soc.* (1981) 103:3185-3191) or using automated synthesis methods. Kinasing of single strands prior to annealing or for labeling may be achieved by using the process of Maniatis et al. supra, or by using an excess, e.g., approximately 10 units of polynucleotide kinase to 1 nM substrate in the presence of 50 mM Tris, pH 7.6, 10 mM $M\lambda Cl_2$, 5 mM DTT, 1-2 mM ATP. If kinasing is for labeling of probe, the ATP will generally contain high specific activity $\alpha$-$^{32}P$.

Ligations are typically performed in 10-30 μl volumes under the following standard conditions and temperatures: 20 mM Tris-Cl pH 7.5, 10 mM $MgCl_2$, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt-end" ligation). Many variations are known to those skilled in the art. Intermolecular "sticky end" ligations are usually performed at 33-100 μg/ml total DNA concentrations (5-100 nM total end concentration). Intermolecular blunt end ligations (usually employing a 1-30 fold molar excess of linkers) are performed at 1 μM total ends concentration.

In vector construction employing "vector fragments," the vector fragment is commonly treated with bacterial alkaline phosphatase (BAP) or calf intestinal alkaline phosphatase (CIAP) in order to remove the 5′ phosphate and prevent religation of the vector. BAP digestions are conducted at pH 8 in approximately 150 mM Tris, in the presence of $Na^+$ and $Mg^{+2}$, using about 1 unit of BAP per mg of vector at 60° C. for about one hour. In order to recover the nucleic acid fragments, the preparation is extracted with phenol/chloroform and ethanol precipitated. Alternatively, religation can be prevented in vectors that have been double digested by additional restriction enzyme digestion of the unwanted fragments.

For portions of vectors derived from cDNA or genomic DNA that require sequence modifications, site-specific, primer-directed mutagenesis is used. This is now a technique that is well-established in the art, and is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature that permits hybridization of an exact match, but at which the mismatches with the original strand are sufficient to prevent hybridization. Plaques that hybridize with the probe are then picked and cultured, and the DNA is recovered.

An alternative preferred method is that of Kramer et al., *Nuc. Acid Res.* (1984) 12:9441-9456, the disclosure of which is incorporated herein by reference. In this method single-stranded DNA and replicative form DNA are annealed together in a gap duplex buffer and the resulting duplex is confirmed and retained for subsequent ligation.

In the constructions set forth below, correct ligations for plasmid construction are confirmed by first transforming *E. coli* strain MM294 (obtainable from *E. coli* Genetic Stock Center, CGSC #6135) or other suitable host, with the ligation mixture. Successful transformants are selected by ampicillin, tetracycline or other antibiotic resistance or using other markers, depending on the mode of plasmid construction, as is understood in the art. Plasmids from the transformants are then prepared according to the method of Clewell, D. B., et al., *Proc. Natl. Acad. Sci.* (*USA*) (1969) 62:1159, optionally following chloramphenicol amplification (Clewell, D. B., *J. Bacteriol.* (1972) 110:667). The isolated DNA is analyzed by restriction enzyme analysis and/or sequenced by the dideoxy method of Sanger, F., et a.l., *Proc. Natl. Acad. Sci.* (*USA*) (1977) 74:5463 as further described by Messing, et al., *Nucleic Acids Res.* (1981) 9:309, or by the method of Maxam, et al., *Methods in Enzymology* (1980) 65:499.

Host strains used in cloning and expression herein are as follows:

For cloning and sequencing, and for expression of construction under control of most bacterial promoters, *E. coli* strain MM294 (supra) or derivatives, Talmadge, K., et al., *Gene* (1980) 12:235; Meselson, M., et al., *Nature* (1968) 217:1110 may be used as the host. For expression under control of the pLNRBS promoter, *E. coli* strain K12 MC1000 lambda lysogen, $N_7N_{53}CI857$ Sus P80 (ATCC 39,531) may be used. Also, *E. coli* DG116, which was deposited with ATCC (ATCC 53,606) on Apr. 7, 1987, may be employed.

For M13 phage recombinants, *E. coli* strains susceptible to phage infection, such as HB2151, HB2154, or *E. coli* K12 strain DG98, are employed. The DG98 strain has been deposited with ATCC on Jul. 13, 1984 and has ATCC accession number 39,768.

For yeast transformations, *S. cerevisiae* strains such as C468 (Innis, M. A. et al., *Science* (1985) 228:21-26) and its cir° derivative may be used. C468 cir° was deposited with ATCC on Dec. 13, 1985 and has ATCC accession number 20,787.

Mammalian expression can be accomplished in COS-7, COS-A2, CV-1, and murine cells, and insect cell-based expression in *Spodoptera frugipeida.*

The hydrophobic recombinant IL-2 produced from transformed bacterial host cells containing recombinant DNA generally aggregates and/or precipitates inside the cell as opposed to being soluble in the cell culture medium. The intracellularly produced protein must be separated from the cellular debris and recovered from the cell before it can be formulated into a purified biologically active material. European Pat. Publication No. 206,828 published Dec. 30, 1986, the entire disclosure of which is incorporated herein by reference, discloses a process for isolating such a refractile material. In this process the cell membrane of the transformed host microorganism is disrupted, greater than 99% by weight of the salts is removed from the disruptate, the desalted disruptate is redisrupted, a material, preferably a sugar such as sucrose, is added to the disruptate to create a density or viscosity gradient in the liquid within the disruptate, and the refractile material is separated from the cellular debris by high-speed centrifugation, i.e., at about 10,000 to 40,000×g. Preferably, the salts are removed from the disruptate by diafiltration or centrifugation and sucrose is added to increase the density of the liquid to about 1.1 to 1.3 g/ml.

After the centrifugation step, the pellet containing the refractile bodies is solubilized with a denaturant such as sodium dodecyl sulfate, the resulting suspension is centrifuged, and the supernatant containing the protein is processed to isolate the protein. The protein is separated from the supernatant by appropriate means such as reverse-phase high pressure liquid chromatography (RP-HPLC) and/or gel filtration chromatography. After such separation, the protein can be processed by disulfide exchange, e.g., using glutathione as described by the following references, the disclosures of all of which are incorporated herein by reference: *Meth. Enzym.* Vol. 131, Enzyme Structure Part L, C. H. W. Hirs, ed. (Academic Press, Inc., New York, 1986) P.83 (Creighton), Snyder, *Biochemistry* (1987) 26:688-694, and Saxena and Wetlaufer, *Biochemistry* (1970) 9:5015.

Alternatively, the separated protein may be oxidized (made to form disulfide bonds) to ensure the production of high yields of recombinant protein in a configuration most like its native counterpart. For example, the $cys_3$IL-2 is preferably not oxidized, whereas the native sequence rIL-2 preferably is oxidized before reaction with the polymer. Such oxidation is described in U.S. Pat. No. 4,530,787 to Z. Shaked et al., the disclosure of which is incorporated herein by reference. The oxidation may also be carried out by reacting an aqueous solution containing a solubilized form of the protein at a pH between about 5.5 and 9 in the presence of air with at least an effective amount of an oxidation promoter containing a $Cu^{+2}$ cation, as described in U.S. Pat. No. 4,572,798 to K. Koths et al., the disclosure of which is incorporated herein by reference. The preferred oxidation promoter or oxidant is $CuCl_2$ or (o-phenanthroline)$_2$ $Cu^{+2}$. After oxidation, the protein may optionally be desalted and purified further by RP-HPLC, dilution/diafiltration, S200 gel filtration chromatography, and ultrafiltration techniques before modification with activated homopolymer as described further hereinbelow.

The polymer modification may be carried out at any step after the heterologous IL-2 protein has been isolated in sufficiently pure form to be biologically active. The point at which the modification will occur will depend, for example, on the ultimate purity of the IL-2 required for the final use thereof, including pharmaceutical formulation.

Guanidine hydrochloride may be used as a denaturant for the solubilization of the particle paste or after the HPLC step, as described more fully in copending U.S. Pat. No. application Ser. Nos. 48,408 and 48,405, both of which were filed on May 11, 1987, and the disclosures of both of which are incorporated herein by reference.

Briefly, U.S. Ser. No. 48,408 describes and claims a process for recovering purified recombinant IL-2 from a transformed microorganism comprising:

(a) disrupting the cell membrane of the microorganism;

(b) separating water-insoluble IL-2-containing material from the disruptate;

(c) mixing the insoluble IL-2-containing material of step (b) at a pH of about 7 to about 9 with an aqueous solution of a reducing agent and a chaotropic agent whereby the IL-2 in the insoluble material is dissolved and denatured;

(d) separating the IL-2 containing solution of step (c) from the undissolved portion of the insoluble material;

(e) removing the reducing agent from the separated IL-2-containing solution;

(f) oxidizing the IL-2 in the solution while maintaining the concentration of chaotropic agent at a strongly denaturing concentration, whereby the natural disulfide bridge of IL-2 is formed (if the IL-2 is $ser_{125}$IL-2);

(g) after the oxidation of step (f) is complete, diluting the solution to reduce the concentration of chaotropic agent in the solution to a level at which the oxidized IL-2 is permitted to renature and a precipitate forms;

(h) separating the precipitate from the solution to provide a supernatant;

(i) purifying the oxidized IL-2 in the supernatant by (1) reverse-phase high performance liquid chromatography followed by a precipitation step and, then, dissolution of the precipitate in a solution of chaotropic agent and removal of the chaotropic agent from the solution, or (2) hydrophobic interaction chromatography followed by ion exchange chromatography; and (j) recovering a purified oxidized, heterologous human IL-2 composition having an IL-2 content of at least about 95% as determined by reducing sodium dodecyl sulfate polyacrylamide gel electrophoresis analysis, a solubility in phosphate buffered saline of at least about 5 mg IL-2 per ml, a specific activity of at least about $1\times10^6$ units/mg as determined by HT-2 cell proliferation assay, and an endotoxin content of less than about 0.1 nanograms of endotoxin per mg of IL-2.

The chaotropic agent is preferably guanidine hydrochloride and the strongly denaturing concentration is preferably at least about 6M.

Briefly, U.S. Ser. No. 48,405 describes and claims a process for recovering recombinant IL-2 from transformed microorganisms containing the IL-2 wherein the IL-2 is separated from the bulk of the cellular components of the microorganisms, solubilized in a reduced form, thereafter oxidized, and thereafter purified to clinically acceptable purity and endotoxin levels, the improvement in which process comprises denaturing the oxidized, purified IL-2 by placing the IL-2 in a solution of a chaotropic agent, removing solids from the solution, and thereafter renaturing the IL-2 from the solution, whereby a renatured, oxidized, purified IL-2 having improved stability and solubility properties in the absence of detergents is obtained. Preferably the solubilization of the reduced IL-2 is achieved by mixing the separated IL-2 with an aqueous solution from 0.1 to 10% (w/v) of sodium dodecyl sulfate. More preferably, the solution of a chaotropic agent is a 4 to 8M aqueous guanidine hydrochloride solution.

The term "selectively conjugated" as used herein to apply to the IL-2 protein refers to IL-2 proteins that are covalently bonded via the sulfhydryl group on one or more targeted cysteine residues of the protein. The cysteine is/are linked to the reactive group of the activated polymer through a thioether bond. Preferably, there is only one such targeted cysteine residue. This provides a specific site of polymer attachment, given that the cysteine residues at positions 58 and 105 of IL-2 are disulfide-bonded, as necessary for full biological activity. Site-directed mutagenesis at desired positions of the recombinant IL-2 primary sequence provides known locations for polymer attachment. For example, one of the amino acids at positions 1–20 at the N-terminus of the native IL-2 sequence (for example, the threonine at position 3) may be replaced with a cysteine residue. This replacement may be the only change from the native sequence or may be one of two or more replacements of amino acids. In the latter instance, the replacements may take place in any order. Additionally, the $cys_{125}$ of the IL-2 molecule may be modified.

The number of polymer molecules conjugated to the protein can be calculated by various methods including, for example, acid degradation or digestion, followed by amino acid analysis if maleimido or bromoacetyl to cysteine links are used. Alternatively, the conjugated protein can be digested into small fragments with an enzyme (e.g., trypsin) and separated by column chromatography. A peptide map of the protein before and after modification would be compared, and fragments with altered elution sequenced to determine the location(s) of polymer attachment(s). In a third alternative, the polymer can be radioactively labeled prior to coupling to determine how many moles of radioactive polymer are attached per mole of IL-2 protein.

According to the process of this invention, the IL-2 is conjugated through a particular linkage to a specified polymer. The pH of the conjugation reaction is preferably 5 to 7, more preferably 5.5–6.

The polymer to which the IL-2 protein is attached is a homopolymer of polyethylene glycol (PEG) or is a polyoxyethylated polyol, provided in all cases that the polymer is soluble in water at room temperature. Examples of polyoxyethylated polyols include polyoxyethylated glycerol (POG), polyoxyethylated sorbitol, polyoxyethylated glucose, or the like.

The glycerol backbone of polyoxyethylated glycerol is the same backbone occurring naturally in, for example, animals and humans in mono-, di-, and triglycerides. Therefore, POG would not necessarily be seen as foreign in the body.

Although the molecular weight of the polymer is not critical, it is preferred that the polymer have a molecular weight between about 300 and 100,000, more preferably between 4000 and 40,000, depending, for example, on the particular protein employed and the number of polymer moieties added.

Preferably the PEG homopolymer is substituted at one end with an alkyl group but it may be unsubstituted as well. Preferably the alkyl group is a $C_1$–$C_4$ alkyl group, and most preferably a methyl group. Most preferably, the polymer is an unsubstituted homopolymer of PEG, a monomethyl-substituted homopolymer of PEG or polyoxyethylated glycerol, and has a molecular weight of about 4000 to 40,000.

The IL-2 protein is conjugated via a terminal reactive group on the polymer. The polymer with the reactive group(s) is designated herein as activated polymer. The reactive group selectively reacts with one or more free cysteine residues on the IL-2 protein, preferably one. To avoid having the reactive group of the polymer react with too many particularly active cysteine groups on the IL-2, it is recommended that the amount of activated polymer employed be no more than 50 moles per mole of IL-2. Most preferably this amount is about to 20 moles per mole of IL-2, depending on the specific properties ultimately desired, i.e., the final amount is a balance to maintain optimum activity, while at the same time maximizing, if possible, the serum half-life of the IL-2 protein. Preferably, at least about 50% of the biological activity of the IL-2 protein is retained, and most preferably 100% is retained.

The covalent modification reaction may take place by any suitable method generally used for biologically active proteins with inert polymers, preferably at about pH 5–7. Generally the process involves preparing an activated polymer (with at least one terminal hydroxyl group) and thereafter reacting the IL-2 protein with the activated polymer to produce the IL-2 protein suitable for formulation.

In a preferred embodiment of the invention, monomethyl (m)PEG-amine is prepared in a first step from a mPEG of 4000 dalton molecular weight or mPEG of 10,000 dalton molecular weight by Gabriel synthesis. Thus, mPEG-OH is converted to mPEG-tosylate and then to mPEG-phthalimide. The phthalimide is cleaved with hydrazine to give mPEG-$NH_2$. In the second step, a maleimido-6-aminocaproic acid-PEG (PEG-sac-mal) reagent is synthesized from the mPEG-$NH_2$ using N-maleimido-6-aminocaproic ester of 4-hydroxy-3-nitrobenzene sulfonic acid (mal-sac-HNSA), HNSA being described by Bhatnagar et al., *Peptides: Synthesis-Structure-Function, Proceedings of the Seventh American Peptide Symposium,* Rich et al. (eds.) (Pierce Chemical Co., Rockford, Ill., 1981), p. 97–100, in Nitecki et al., *High-Technology Route to Virus Vaccines* (American Society for Microbiology: 1985), pages 43–46 (based on talk Nov. 8–10, 1984) entitled "Novel Agent for Coupling Synthetic Peptides to Carriers and Its Application," and in Aldwin et al., *Anal. Biochem.* (1987) 164:494–501, the disclosures of which are incorporated herein by reference. The PEG-sac-mal reagent is then covalently conjugated to the IL-2 protein of choice.

The IL-2 protein thus modified may then be formulated in a non-toxic, inert, pharmaceutically acceptable aqueous carrier medium, preferably at a pH of about 5 to 8, more preferably 6–8. For in vitro applications, as for IL-2 used for diagnostic purposes, the modes of administration and formulation are not as critical. Lyophilized formulations compatible with the culture or perfusion medium will generally be used. When used in vivo for therapy, the sterile product will consist of IL-2 protein in an aqueous buffer in an amount that will provide a pharmaceutically acceptable pH when the formulation is lyophilized and reconstituted. The lyophilized formulation may be reconstituted by injecting into the vial a conventional parenteral aqueous injection such as, e.g., distilled water. A water-soluble carrier such as mannitol may optionally be added to the medium. The currently formulated lyophilized unmodified IL-2 is stable for at least six months at 4° C.

The dosage level of IL-2 protein in the formulation will depend on the in vivo efficacy data obtained after preclinical testing and will depend mainly on the ultimate use.

The reconstituted formulation prepared as described above is suitable for parenteral administration to humans or other mammals in therapeutically effective amounts (i.e., amounts that eliminate or reduce the patient's pathological condition) to provide therapy thereto. IL-2 therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell-mediated anti-tumor activity.

As an alternative to administration of IL-2 alone, the IL-2 may be administered in an adoptive immunotherapy method, together with isolated, lymphokine-activated lymphocytes, in a pharmaceutically acceptable carrier, where the lymphocytes are reactive to tumor when administered with the IL-2 to a human suffering from the tumor. This method is described more fully in U.S. Pat. No. 4,690,915 issued Sep. 1, 1987 and by S. Rosenberg et al., *New England Journal of Medicine* (1985), 313:1485–1492. Alternatively, the IL-2 may be used in conjunction with tumor-infiltrating lymphocytes (TIL) as described by Rosenberg et al., *Science* (1986) 233:1318–1321.

The dose and dosage regimen of the IL-2 will depend, for example, on the pharmacokinetics of the drug, the nature of the disease, the characteristics of the IL-2, the patient and the patient's history. For example, different modified IL-2 proteins are expected to have different pharmacokinetic and therapeutic properties that are advantageous for different routes of administration. A long-acting drug might only be administered every 3–4 days, every week or once every two weeks. The clearance rate can be varied to give ultimate flexibility to fit the particular need of the patient by changing, e.g., the type of polymer and the size of the polymer attached.

In the following examples, which illustrate the invention further, all parts and percentages are by weight unless otherwise noted, and all temperatures are in degrees Celsius.

EXAMPLE I

Preparation of PEGylated IL-2 Mutein With 4,000 Molecular Weight PEG

A. Preparation of PEG-Maleimide Reagent.

1. Preparation of PEG-4000-$NH_2$ (PEG-Amine)

Monomethyl PEG-4000 (from Union Carbide), 6.0 g (1.5 mmole), was first dissolved in 10 ml methylene chloride and then 1.8 ml (22.2 mmole) pyridine and 6.0 g (31.6 mmole) p-toluenesulfonyl chloride were added. The flask was flushed with nitrogen and the reaction mixture stirred at room temperature overnight. The mixture was concentrated to about 5 ml and the product precipitated with 75 ml ethyl ether. The precipitate was collected and washed with ether. The product was recrystallized from ethanol and the yield was 6.0 g mPEG-tosylate.

The mPEG-tosylate (6.0 g, about 1.5 mmole) was dissolved in 20 ml dimethylformamide and 2.5 g (17.0 mmole) potassium phthalimide was added. The solution was heated at reflux under nitrogen for four hours. The precipitate that formed was filtered off and the filtrate was added dropwise to 300 ml ether to precipitate the product. The precipitate was filtered and washed with ether. The product was suspended in 30 ml methylene chloride and stirred for 0.5 hours. Insoluble impurities were filtered off and the product was precipitated with ether. The yield was 4.4 g mPEG-phthalimide. Next, mPEG-phthalimide (4.4 g, ~1.1 mmole) was dissolved in 15 ml ethanol and 2.0 ml (41.2 mmole) hydrazine hydrate was added. The mixture was refluxed overnight. The reaction mixture was cooled to room temperature and the product was precipitated with ether.

The precipitate was collected by filtration and resuspended in 25 ml methylene chloride. Insoluble impurities were filtered off and the product was precipitated with ether. This precipitate was suspended in $CH_2Cl_2$, filtered, and precipitated with ether two more times. The second time it was completely soluble in methylene chloride. The yield was 3.5 g mPEG-4000-amine.

2. Preparation of maleimido-6-aminocaproyl ester of HNSA (mal-sac-HNSA).

The 1-hydroxy-2-nitrobenzene-4-sulfonic sodium salt (HNSA) was synthesized according to the procedure of Ghehm and Knecht, *J. Prakt Chemie* (1906) 73:519-537, the disclosure of which is incorporated herein by reference. Maleimido-6-aminocaproic acid (mal-sac) was formed by refluxing 20 g of maleoyl-6-aminocaproic acid solution in 500 ml of acetic acid for 24 hours. Acetic acid was removed in vacuo and the oily residue was dissolved in 100 ml of chloroform. The uncyclized maleoyl-6-aminocaproic acid precipitated overnight at room temperature. The mother liquid was concentrated to a small volume and chromatographed over a silica gel column, 600 ml bed volume, in chloroform:acetic acid (95:5). The best fractions were combined and the solvent was removed, yielding approximately 9 g. After recrystallization from 30 ml of warm chloroform, thin layer chromatography on silica gel plates (diisopropyl ether:chloroform:acetic acid (6:3.1) and chloroform:acetone:acetic acid (50:50:1)) was performed. Detection was achieved by iodine vapors, UV absorbance, or a spray specific for the maleimido group (Kelkle and Rundinger, *Helv. Chim. Acta* (1975) 58:531-541).

Next, 2.42 g (100 mmol) of HNSA was dissolved in 10 ml dimethylformamide (DMF) and 2.1 g (100 mmol) of mal-sac was added. Dicyclohexylcarbodiimide, 2.06 g (100 mmol) was dissolved in 4 ml DMF and added to the above. Within 10-15 minutes, the insoluble dicyclohexylurea began to appear. After several hours reaction at room temperature, the urea was filtered and the mother liquor treated with 200 ml dry ether. The precipitated yellow oil was triturated with fresh ether until it solidified. The crude product was dried in vacuo. The yield was 3.7 g, which contained 85% ester, assayed as described below. The ester can be dissolved in water and rapidly lyophilized for easier handling.

The analysis consisted of dissolving a small amount of the lyophilized solid in phosphate buffer at pH 7.0 and measuring absorbance at 406 nm; this reading provides the amount of unreacted free HNSA that is the contaminating material in the HNSA ester preparation. Addition of very small amounts of concentrated strong base (such as 5N NaOH) instantly hydrolyzed the ester, and an increased absorbance at 406 nm was recorded. Subtraction of the first reading from the second yields the amount of ester in the original material.

The ester thus obtained was found to dissolve in water up to 1.0M concentration and was found to be stable in water for several hours, provided no nucleophiles were added. The purified ester was found to be stable for extended periods when stored dessicated.

3. Synthesis of PEG-4000-$NH_2$-sac-mal.

About 100 mg of PEG-4000-$NH_2$ (25 μmole) was dissolved in 2.5 ml of 0.1 phosphate buffer, pH 7.5, to make a solution 0.01M in PEG-$NH_2$. Next, 59 mg of the mal-sac-HNSA (137 μmole), an approximately 5-fold excess over PEG-$NH_2$, was added to the PEG-$NH_2$ solution and stirred at room temperature. The reaction was monitored by diluting 5 μl aliquots to 1.0 ml of 0.01M phosphate buffer, pH 7.0 and recording the absorbance at 406 nm. Any remaining ester was completely hydrolyzed upon the addition of 50 μl of 5N NaOH and absorbance at 406 nm was recorded. The reaction was complete in 35 minutes, at which time 57% of the PEG-4000-$NH_2$ had acquired a mal-sac group.

The PEG-4000-$NH_2$-sac-mal was separated after 90 minutes of reaction on a Sephadex G-25 desalting column run in water. Fractions containing the large molecules were pooled and lyophilized, yielding approximately 90 mg of powder.

B. Preparation and Purification of IL-2 Mutein

Various embodiments of IL-2 muteins and the techniques used to construct the respective genes encoding these muteins have been disclosed in the literature. For example, the construction of des-$ala_1ser_{125}$IL-2 is described in U.S. Pat. No. 4,518,584 and the techniques used to construct this gene and express the resulting IL-2 mutein are described in U.S. Pat. No. 4,588,585. Both of these patents are assigned to Cetus Corporation and the disclosures of each are incorporated herein by reference.

The approximately 440 base pairs (bp) HindIII, StuI restriction fragment containing the des-$ala_1ser_{125}$IL-2 DNA sequence was subcloned from plasmid pLW45 into HindIII, HincII-digested M13mp9 replicative form (RF) (available from the American Type Culture Collection, Rockville, Md. (ATCC)). A sample of *E. coli* K12/MM294-1 carrying plasmid pLW45 was deposited in the American Type Culture Collection on Mar. 4, 1984 under accession number 39,626. Single-stranded phage DNA was prepared essentially by the method of Sanger et al., *J. Mol. Biol.* (1980) 143:161-178, the disclosure of which is incorporated herein by reference, from one of the resulting clones containing the IL-2 insert sequence to serve as a template for oligonucleotide-directed mutagenesis.

About 31 μg of M13mp19 RF DNA available from Bethesda Research Laboratories was digested with HindIII and EcoRI restriction enzymes. The enzymes were heat denatured at 66° C. for five minutes. Then 20 units of T4-DNA polymerase (3'-5' exonuclease) was added according to T. Maniatis, *Molecular Cloning: A Laboratory Manual* (1982) page 121, the disclosure of which is incorporated herein by reference, to digest away the small 48 bp fragment from the 3' ends. The reaction was terminated after 10 minutes at 37° C. by the addition of a several-fold molar excess of all four dNTPs. This addition also initiates the repair function of T4-DNA polymerase to produce the 7220 bp blunt-end repaired fragment of interest (reaction for one hour at 37° C.).

Next, approximately 1 picomole (pmole) of the single-stranded M13mp9 DNA and approximately 0.2 pmole of the RF M13mp19 DNA prepared above were annealed together in the gap duplex buffer essentially according to the gap-duplex method of Kramer et al., supra. An aliquot of the resulting duplex was confirmed on a 1% agarose minigel and the bulk retained for subsequent ligation to a kinased primer.

A 38-mer oligonucleotide primer of the sequence 5'-GCTGTGTTTTCTTTGTAGAGCT-CGAACAAGGCATAAGC-3' was chemically synthesized using a Biosearch Model 8700 DNA synthesizer using controlled-pore glass and o-cyanoethyl-N,N-diisopropyl phosphoramidites (Beaucage et al., *Tet. Lett.* (1981) 22:1859–1862 and Sinha et al., *Nuc. Acid Res.* (1984) 12:4539–4557. This primer was designed to replace threonine at position 3 of the native IL-2 DNA sequence with cysteine, as well as to introduce a unique SacI restriction site for identification purposes. About 200 pmoles of the 38-mer primer were kinased in the presence of at least a 2–3 fold molar excess of ATP, 10×kinasing buffer and 5 units of T4 kinase in approximately 30 μl at 37° C. for 45 minutes. The reaction was stopped by heat denaturing at 65° C. for five minutes, and the kinased primer was diluted 1:3 in $H_2O$. About 20 pmole of the kinased primer was annealed to 0.05 pmoles of the gapped duplex, by heating at 65° C. for three minutes and then cooling to room temperature for 30 minutes. The gapped duplex and primer were adjusted to approximately 140 μl final volume of a reactive mixture containing primer extension ligation (PEL) buffer (at a final concentration of 0.1M KCl, 0.03M Tris, pH 7.5, 0.015M $MgCl_2$, and 0.002M dithiothreitol), 0.25 mM of each dNTP, 53 μM ATP, 68 μl $H_2O$, 20 units of DNA polymerase I Klenow fragment, and 140 units of T4 DNA ligase, and incubated overnight at 16° C.

The reaction mixture was used to transform competent *E. coli* HB2154 (Mutl−, sup−) cells (a derivative of *E. coli* HB2151 (sup−) cells and available from Anglian Ltd., England). The transformed HB2154 cells were then plated with a top agar overlay containing *E. coli* HB2151 (sup−) cells (also available from Anglian Ltd.) and incubated overnight to obtain phage plaques. DNA minipreparations were made from the phage plaques by inoculating fresh overnight cultures of *E. coli* HB2151 cells and adding one plaque/tube from the previous transformations, using a method modified from Maniatis, supra.

Screening and identification of the mutagenized phage plaques were carried out as follows:

A double restriction digest using SacI and BamHI was used to drop out an approximately 450 bp fragment in those clones containing the engineered unique SacI site. Twenty-two out of twenty-four clones screened had the appropriate restriction pattern. Three of these were chosen for DNA sequence analysis using the dideoxynucleotide chain termination method of Sanger et al., *Proc. Natl. Acad. Sci.* (*USA*) (1977) 74:5463–5467. The analysis confirmed the thr to cys mutation in all three clones tested.

One of the resulting clones was chosen for subcloning the mutagenized IL-2 gene into pPLOP (ATCC No. 39,947), an *E. coli* expression vector wherein the gene expression is driven by the $P_L$ promoter.

The plasmid pPLOP was cut with the restriction enzymes BamHI and HindIII. This material was then dephosphorylated with bacterial alkaline phosphatase (BAP) to prevent self ligation. The BAP was removed by phenol extraction. Clone #19 RF DNA was digested with BamHI and HindIII and cleaned up prior to shotgun subcloning into the pPLOP plasmid treated with BAP. The ligation mix was used to transform competent *E. coli* DG95 cells, a lambda lysogen (ATCC No. 39,768 deposited Jul. 13, 1984). The plasmid DNA from the resulting transformants were analyzed by restriction enzyme mapping using HindIII and BamHI to drop out the approximately 440 bp IL-2 sequence. Eleven of twelve screened contained the correct size insert.

The $cys_3$ IL-2 mutein was expressed in DG95 λ lysogen cells. Cells were grown at 30° C. until the absorbance at 600 nm reached 1.0, and they were then shifted to 42° C. to simultaneously amplify plasmid copy number and derepress the $P_L$ promoter. The cells were then concentrated with a concentrator and diluted to 10% volume with 50 mM Tris pH 8.0, 1 mM EDTA.

The cells were then sonicated to 20% of the original absorbance at 600 nm. There were no intact cells remaining and the resultant mixture was centrifuged down 8,000×g for 20 minutes at 4° C. The pellet was suspended in a solution containing 35% sucrose (w/w) and 10 mM EDTA. This suspension was centrifuged at 8,000×g for 15 minutes at 4° C. The pellet was then resuspended in 10 mM EDTA, pH 8.0 and recentrifuged at 8,000×g for 15 minutes at 4° C. The supernatant was discarded and the pellet was frozen at −20° C. and stored for 48 hours.

The frozen pellet was solubilized in 10% SDS in Buffer K (50 mM sodium acetate pH 5.5, 0.1% SDS, 1 mM EDTA) and 100 mM dithiothreitol. This suspension was then centrifuged at 25,000–35,000×g and the supernatant was checked to see if inclusion body debris was removed. As the debris was removed, the supernatant was loaded on a Sephacryl S200 column in Buffer K. The S200 peak was pooled and concentrated from 25 ml down to 1.5 ml on a PMIO membrane.

The 1.5 ml S-200 pool was mixed with Solvent A (10% $CH_3CN$, 0.1% trifluoroacetic acid) and loaded on a Vydac C4 HPLC column. Three peaks, x, y and z, were collected, and peak y was chosen for further purification. Peak y was lyophilized and resuspended in Solvent A and 0.5 mM DTT and then loaded (~630 μg) on a Vydac C18 RP-HPLC column. A single peak was collected.

The single peak was assayed for bioactivity using the IL-2 cell proliferation bioassay in vitro described by Gillis et al., *J. Immunol.* (1978) 120:2027–2032, and found to be active.

C. Conjugating of PEG-4000 Maleimide Reagent to IL-2

Reduced, lyophilized des-$ala_1cys_3ser_{125}$IL-2 (designated hereafter as cys3IL-2) (0.54 mg/ml) in a buffer consisting of 50 mM sodium acetate, pH 5.5 and 0.1% (w/v) SDS was reacted with an equimolar amount of PEG-mal-sac. The reaction mixture was stirred at room temperature and monitored by size-exclusion-HPLC on a TSK 250 column run in the same buffer. The sample was quenched with DTT prior to loading on a TSK 250 column. Three fractions were pooled from the TSK column and assayed for bioactivity as described by Gillis et al., supra. The activities of the PEGylated IL-2 were $3.5-4\times10^6$ units/mg, which is comparable to that of the unmodified starting material. Fractions that had oligomerized had reduced activity.

The site-specific PEGylation (of one cysteine of the IL-2) resulted in retention of bioactivity.

EXAMPLE II

Preparation of PEGylated IL-2 Mutein with 10,000 Molecular Weight PEG

A $cys_3$IL-2 derivative of linear, monomethyl substituted PEG of molecular weight 10,000 was obtained generally following the methods described below. Monomethyl PEG (10,000), from Union Carbide, 6.0 g, was dissolved in 30 ml $CH_2Cl_2$ and then 5.0 g tosyl chloride and 1.5 ml pyridine were added. After stirring overnight at room temperature the solution was concentrated to 15 ml, then the product was precipitated with ether. The product was recrystallized from ethanol. The yield was 5.4 g mPEG-tosylate.

The mPEG-tosylate (5.4 g) was dissolved in 25 ml DMF and 2.0 g potassium phthalimide was added. After refluxing for four hours the precipitate that formed was filtered off. The product was precipitated with ether. The crude product was suspended in 200 ml $CH_2Cl_2$ and stirred for 0.5 hours. Insoluble impurities were removed by filtration and the filtrate was concentrated to 30 ml. The product was precipitated with ether and the yield was 3.0 g mPEG-phthalimide.

Next, mPEG-phthalimide (3.0 g) was dissolved in 15 ml ethanol and 1.5 ml hydrazine hydrate was added. The solution was refluxed overnight. After cooling to room temperature, the product was precipitated with ether. The product was suspended in 100 ml $CH_2Cl_2$ and stirred for 0.5 hours, then filtered. The filtrate was concentrated to 20 ml before precipitation with ether. This product dissolved completely in 70 ml $CH_2Cl_2$. The solution was concentrated to 20 ml and the product precipitated with ether. The yield was 1.5 g mPEG 10,000-amine.

The mal-sac-HNSA prepared in Example 1.A.3 was reacted with the mPEG-10,000-amine according to the teaching of Example I.A.3 to form the mPEG$\sim$10,000-$NH_2$-sac-mal reagent. The extent of modification was 48% by weight. This reagent was conjugated to the $cys_3$IL-2 according to the teaching of Example I.C., except that a 10-fold molar excess of mPEG 10,000-maleimide reagent to the IL-2 mutein was used.

EXAMPLE III

Preparation of PEGylated Native Sequence IL-2

A. Preparation

Recombinant human IL-2 that lacks the initial N-terminal alanine of the native molecule and has a cysteine residue at position 125 was prepared using the plasmid pLWI cloned into M13mp9 as described in U.S. Pat. No. 4,518,584 issued May 21, 1985, the disclosure of which is incorporated herein by reference. A sample of pLWI was deposited in the American Type Culture Collection on Aug. 4, 1983 and has ATCC No. 39,405. The resulting IL-2 protein was isolated and purified as described in copending U.S. application Ser. No. 843,997 filed Mar. 25, 1986, supra, the disclosure of which is incorporated herein by reference.

Briefly, the cells, transformed with pBR322 carrying the relevant gene and under the trp promoter, were grown at 37° C. in a growth medium. The cells containing refractile bodies with the protein were concentrated about 10-fold by cross-flow filtration and then disrupted in the presence of 1-octanol. Then distilled water was added to the disruptate, which was diafiltered against deionized water and the cells were redisrupted. Then sucrose was added to a final density of 1.1–1.25 g/$cm^3$. After this, the mixture was centrifuged at high speed and the particle pellet solubilized with about 2% SDS in aqueous phosphate buffered saline (PBS) at 45°–55° C. and at pH 8.5–9.5 in the presence of 5–20 mM DTT and about 2 mM EDTA. Then the suspension was adjusted to pH 7–7.8 and extracted with 2-butanol in a volume ratio of about 0.8:1 to 3:1 2-butanol:suspension and the solids were obtained by acid precipitation in the presence of SDS, DTT and PBS (pH 5–6.5). Then the mixture was centrifuged at 10,000–15,000$\times$g for two to six hours.

The final pellet obtained was solubilized in PBS with 5% SDS desired IL-2 protein was then reduced by adding solid DTT to 50 mM and ethylenediamine tetraacetic acid (EDTA) to 2 mM. The pH was adjusted to about 8.5 and the solution heated to 45°–55° C. for 20 minutes under $N_2$. The pH was then readjusted to about 5.5.

Higher molecular weight contaminants were removed by chromatography with a Sephacryl® S-200 column. Peak fractions were pooled and oxidized with cupric chloride in accordance with U.S. Pat. No. 4,572,798, the disclosure of which is incorporated herein by reference.

The oxidized IL-2 was concentrated using a hollow fiber ultrafiltration unit with a 10,000 molecular weight cut-off. The protein was diafiltered and the pH of the resulting material was lowered to 3 or less.

The IL-2 was then loaded on a preparative HPLC column and eluted with a gradient of 2-propanol in acetic acid. Pooled protein was diluted into a buffer of acetate, pH 5.5, EDTA and SDS. The diluted HPLC pool was concentrated using a hollow-fiber ultrafiltration unit with a 10,000 molecular weight cutoff, and the concentrate was then diafiltered.

The IL-2 was then loaded on a second Sephacryl® S-200 column and eluted with a buffer of acetate, pH 5.5, EDTA and SDS, and IL-2 monomer fractions were pooled. The protein was diafiltered against 10 mM sodium phosphate until the SDS level was 100–200 µg/mg protein.

A 20-fold molar excess of mPEG-4000-$NH_2$-sac-mal reagent was added to 0.5 ml of 1.0 mg/ml of the des-$ala_1$IL-2 described above. The des-$ala_1ser_{125}$IL-2 was used as a control, using the same reaction conditions. The reaction mixtures were stirred at 22°–24° C. for 38 hours. Then 0.45 ml of the reaction mixture was diluted two-fold in reverse-phase Solvent A (10% $CH_3CN$, 0.1% trifluoroacetic (TFA)), injected onto a Vydac C18 column, and eluted with a gradient of acetonitrile in 0.1% TFA. Protein peaks, identified by their UV/visible absorbance spectra, were lyophilized and analyzed for bioactivity by the cell proliferation assay method of Gillis et al., *J. Immunol.* (1978) 120:2027–2032 (the disclosure of which is incorporated herein by reference), and for SDS-PAGE migration. There was no modification with PEG observed in the control, des-$ala_1ser_{125}$IL-2, under these conditions.

The RP-HPLC elution of the reaction mixture showed a baseline resolution of modified from unmodified des-$ala_1$IL-2; these two molecules were identified by PHAST (8-25% acrylamide gradient) SDS-PAGE. The single mPEG-mal-IL-2 peak from HPLC migrated as a single band on both reducing and non-reducing SDS-PAGE. Five samples each of IL-2 and mPEG-mal-IL-2 had average specific bioactivities of $5.10\times10^6$ Cetus units/mg ($11.73\times10^6$ BRMP units/mg) and $2.55\times10^6$ Cetus units/mg ($5.87\times10^6$ BRMP units/mg), respectively, by the cell proliferation assay of Gillis et al., supra.

EXAMPLE IV

Preparation and Purification of Cys31L-2 in Yeast

The following specific example is used to illustrate additional applications of the invention herein for producing alternative active forms of IL-2 in a host other than *E. coli. IL*-2 muteins were produced in *S. cerevisiae* and secreted into the culture medium in correctly folded form. In this example, coding sequences having appropriate substitutions to generate any one of several muteins were ligated into a yeast expression vector utilizing the yeast alpha-1 mating factor promoter, leader, and terminator sequences, and used to produce the desired proteins in yeast.

Specifically, $cys_3ala_{104}$IL-2 and $cys_3ala_{104}$ala125IL-2 muteins of mature human wild-type IL-2 were prepared by site-specific mutagenesis using an M13 cloned reference protein sequence, prepared substantially as described in U.S. Pat. No. 4,518,584, issued May 21, 1985, the disclosure of which is incorporated herein by reference.

Briefly, the IL-2 gene from the plasmid pLW32, which was deposited at the American Type Culture Collection on Dec. 13, 1985 and assigned ATCC No. 53,354, was excised as a HindIII-StuI fragment (Wang, A., et al. (1984) *Science* 224:1431-1433; the StuI site is located some 132 bp upstream from the BamII site). A HindIII linker was added to the blunt StuI end of the fragment. This provided a HindIII fragment containing the IL-2 gene for insertion into an M13mp7 vector that had been modified as follows.

An approximately 1.5 kb EcoRI fragment containing the yeast mating factor (MF) alpha 1 gene (Singh, A. et al. (1983) *Nucleic Acids Res.* 11:4049-4063) from which the HindIII to SalI fragment (nucleotides 268 to 533 in FIG. 3 of their publication) had been deleted to remove the coding sequence for the four copies of the mature alpha-factor, was inserted between the EcoRI sites of M13mp7. Ligation of the HindIII end located 3' of the alpha-factor leader sequence (nucleotide 267) to the repaired SalI end following the fourth copy of the mature alpha-factor coding sequence (nucleotide 534) resulted in the creation of a unique HindIII site in the modified M13mp7 vector (and deletion of the mature alpha-factor coding sequences as just mentioned). The thus-modified M13mp7 was designated M13mp7::MFalpha-delta and contained the yeast alpha factor promoter, leader, and terminator sequences with a unique HindIII site between the leader and terminator into which a gene of interest could be inserted. M13mp7::MFalpha-delta was deposited at the American Type Culture Collection on Dec. 13, 1985 and assigned ATCC No. 40,210.

The HindIII fragment carrying the IL-2 gene previously described was then inserted into M13mp7::MFalpha-delta at its unique HindIII site. An oligonucleotide primer of the following sequence 5'-CTTTGGATAAAAGAGCGCCTACTTCAAG-3' was utilized to delete some 16 nucleotides in order to bring the alpha-factor leader peptide sequence and the IL-2 coding sequence into juxtaposition such that the amino acid sequence at the junction was Lys Arg Ala, which can be correctly recognized as a processing site. The resulting construct was designated M13mp7::MFalpha-delta (IL-2), deposited on Dec. 13, 1985 at the ATCC and assigned ATCC No. 40,211.

$Ala_{104}$-containing muteins of IL-2 in yeast were obtained by site-specific mutagenesis using single-stranded DNA of M13mp7::MFalpha-delta (IL-2) as template. To convert the methionine at position 104 to alanine, the oligonucleotide 5'-ACAACATTCGCTTGTGAATATG-3' was synthesized and employed in a procedure described in U.S. Pat. No. 4,518,584, supra. The threonine at position 3 was converted to cysteine using the oligonucleotide primer 5'-AGAGCGCCATGTTCAAGTTC-3' under the same conditions. The cysteine at position 125 was converted to alanine using the oligonucleotide primer 5'-GATTACCTTCGCTCAAAGCATC-3' under the same conditions. To produce genes containing more than one modification, successive rounds of mutagenesis, each using the appropriate primer, were carried out. These mutations were all confirmed by DNA sequencing of the mutant phage.

Following mutagenesis and selection of the correctly modified coding sequences in M13mp7::MFalpha-delta (IL-2), the EcoRI fragments carrying the alpha-factor promoter, secretory leader, modified IL-2 genes and alpha-factor terminator were removed from the M13 RF DNAs, and the EcoRI ends were made blunt by repair with the large fragment of *E. coli* DNA polymerase I (Klenow fragment) in the presence of the four deoxyribonucleotides (dNTPs), using the method described generally in Maniatis et al., *Molecular Cloning: A Laboratory Manual* (New York:Cold Spring Harbor Laboratory, 1982), pp. 280-281, the disclosure of which is incorporated herein by reference.

After DNA polymerase I repair, the blunt-ended fragment containing the IL-2 mutein genes was ligated using blunt-end conditions and T4 DNA ligase into pJDB219 between the two TthI sites thereof, thereby replacing the TthI/TthI vector fragment. This plasmid, pJDB219, capable of replicating in both *E. coli* and yeast, has been described by Beggs, J. D., *Nature*, 275:104-109 (1978), the disclosure of which is incorporated herein by reference, and its two TthI sites are located in a nonessential region of the portion of the plasmid originally derived from *E. coli* plasmid pMB9. The plasmid construct that resulted, containing the gene coding for the $cys_3ala_{104}$IL-2 mutein, was designated pPM44 and was deposited at the American Type Culture Collection on Dec. 13, 1985 and assigned ATCC No. 53,357.

pPM44 was transformed into polyethylene glycol (PEG)-treated *S. cerevisiae* strain C468 cir° as detailed below to generate a leu+ phenotype. Cells to be transformed were prepared substantially as described in Klebe, R. J. et al. (1983) *Gene*, 25:333-341, the disclosure of which is incorporated herein by reference. Briefly, a single colony was picked into 2 ml YEPD (10 g/l yeast extract; 20 g/l peptone; 2% glucose) and grown overnight at 30° C. The overnight culture was diluted 80-fold into fresh YEPD to provide 10 ml of diluted culture per transformation. Cultures were grown at 30° C. to $A_{600}$ nm=0.6-0.9, usually about 3-3.5 hrs. Cells were pelleted by a 5 min centrifugation at 4000 rpm (Beckman JA-20 rotor) at room temperature. Cell pellets were each resuspended in 5 ml SBEG (1 M sorbitol, 20 mM bicine pH 8.35, 3% ethylene glycol) and centrifuged again. Cell pellets were each resuspended in 0.2 ml SBEG for 5 min at room temperature. Five to ten μg of transforming DNA was added in no more than 20 μl and the mixture was incubated 10 min at 30° C. The mixture was frozen at −70° C. for at least 10 min. The mixture was thawed in a 37° C. bath and 1.5 ml PEG-bicine (40% PEG-1000., 200 mM bicine pH 8.35) was added. After mixing gently, the transformations were incubated 60 min at 30° C. With gentle mixing, 3 mls NB (150 mM NaCl; 10 mM bicine pH 8.35) was added slowly, and the cells were pelleted by centrifugation in a tabletop centrifuge for 3 min at 2000 rpm. Finally, cells were resuspended in 1 ml NB and plated directly on selective medium (in this case 1.45 g/l Yeast Nitrogen Base (Difco); 0.04 M $(NH_4)_2SO_4$; 2% glucose; amino acids minus leucine).

To assay the IL-2 bioactivity of yeast transformants, single yeast colonies from selective plates were picked into 3 ml of either selective or non-selective medium and incubated overnight with shaking at 30° C. An aliquot of the culture was removed and filtered through a 0.2 micron filter (Gelman acrodisc) to remove all yeast cells. Supernatants were diluted without further treatment for assay of biological activity using the standard in vitro HT-2 cell proliferation assay. The mutein was shown to yield equivalent specific bioactivity to that of native IL-2 expressed in the same vector and host, which latter construct, with plasmid pPM42, was deposited at the ATCC on Dec. 13,, 1985 and assigned ATCC No. 53,355. The pPM42 had 5980 BRMP units IL-2/ml (one transformant) and the pPM44 ($cys_3ala_{104}$IL-2) had 7820 BRMP units IL-2/ml (average of two transformants).

A 10-liter fermenter was prepared containing the following medium:

| | |
|---|---|
| 15% glucose | 10 ng/ml D-Biotin |
| 4.0 g/l $NH_4Cl$ | 1 μg/ml Calcium Pantothenate |
| 5 mM $H_3PO_4$ | 40 μg/ml Myo-inositol |
| 3 mM $H_2SO_4$ | 0.5 μg/ml Pyridoxine HCl |
| 5 mM KCl | 1 μg/ml Thiamine HCl |
| 1 mM NaCl | 0.5 mg/ml Histidine |
| 1 mM $MgC1.6H_2O$ | |
| 10 μM $MnSO_4.H_2O$ | |
| 1 μM $CuSO_4.5H_2O$ | |
| 5 μM $ZnSO_4.7H_2O$ | |
| 5 μM $CoCl_2.6H_2O$ | |
| 5 μM $Na_2MoO_4.2H_2O$ | |
| 50 μM $H_3BO_3$ | |
| 100 μM $CaCl_2.2H_2O$ | |
| 40 μM $FeSO_4$ | |

A 50 ml-seed culture of the yeast transformed with pPM44 was grown in the above medium to an optical density at 680 nm of approximately 10. The 10-liter fermenter was inoculated with the seed culture and grown for approximately 40 hours at 30° C. The pH was maintained at 4.5 by addition of NaOH from a 2.5N stock solution. The culture was harvested at an optical density at 680 nm of 29. The yeast cells were removed from the culture by centrifugation and the supernatant was retained. EDTA (0.25M stock) was then added to 10 mM to minimize proteolysis and retard the metal-catalyzed oxidation of free sulfhydryl groups. Sodium acetate (pH 4.5, 3M) was added to a final concentration of 0.1M to help maintain the pH at 4.5 and decrease the possibility of thio-disulfide exchange reactions. The supernatant was first concentrated to 1 liter using an Amicon H10P10-20 hollow fiber cartridge and then further concentrated to 50 ml using an Amicon H1P10-20 hollow fiber cartridge. The culture was then concentrated to approximately 20 ml using a 350-ml Amicon ultrafiltration cell fitted with a PM-10 membrane. After addition of SDS to 2%, the preparation was heated to 37° C. for 15 min. and loaded onto a 5.0×90 cm Sephacryl-200 column previously equilibrated in 100 mM sodium acetate, 100 mM NaCl, 1 mM EDTA and 0.1% SDS (pH 4.5). The column was loaded and run at a flow rate of 1.5 ml/min. The fractions containing IL-2 were identified by IL-2 bioactivity. The major IL-2 activity peak eluted significantly later than the majority of the contaminating proteins, at a position that corresponded to the molecular weight of monomeric IL-2. The activity peak was pooled and concentrated by ultrafiltration using an Amicon cell and a PM-10 membrane. Two-thirds of the S-200 IL-2 pool was loaded onto a 4.6×250 mm Vydac C4 reversed-phase column equilibrated in 30% (w/v) acetonitrile, 0.1% (w/v) trifluoroacetic acid (TFA). The IL-2 was eluted with a linear gradient of 30–60% (w/v) acetonitrile over 45 min. The IL-2 peak, which eluted late in the gradient (similar to other unmodified forms of IL-2), was pooled and stored at 4° C. in acetonitrile and 0.1% TFA.

The purified IL-2 mutein was found to be fully active by the bioassay described above, having a specific activity essentially equivalent to native IL-2 or recombinant IL-2 from *E. coli. N-terminal sequencing showed the IL*-2 contained the native mature sequence beginning ala, pro, thr, etc. The protein was disulfide-bonded and exhibited the expected RP-HPLC retention time.

One half of the RP-HPLC pool (0.85 ml) was then diluted into buffer (2 ml final volume) containing a 100-fold excess (1.66 mg) of PEG-maleimide reagent. Final buffer concentrations were: 20 mM sodium phosphate (pH 6.8), 0.1% SDS, 0.5 mM EDTA, 50 mM NaCl, 15% acetonitrile, and 0.02% TFA. The reaction with the PEG reagent was allowed to continue for 20 hours at 23° C. As a control, $ala_{104}$IL-2, purified in a similar manner as $cys_3ala_{104}$IL-2, was also reacted with the PEG reagent under the same reaction conditions as $cys_3ala_{104}$IL-2. Samples were taken from both reactions and analyzed by size-exclusion HPLC (SEC-HPLC) and SDS-PAGE analysis.

After 20 hours of reaction, SEC-HPLC analysis indicated that the majority of the $cys_3ala_{104}$IL-2 had been converted to a larger molecular weight form, eluting at the position expected for PEGylated IL-2 and for IL-2-IL-2 dimers. The $ala_{104}$IL-2, however, was not significantly affected by the reaction with the PEG reagent, and eluted at the position expected for monomeric, unmodified IL-2.

Reducing SDS-PAGE analysis of the reactions with PEG reagent indicated that the $cys_3ala_{104}$IL-2 had been modified to a greater extent than $ala_{104}$IL-2, indicating that specific attachment of the PEG at the cysteine residue at position 3 had occurred. The small amount of modification observed with $ala_{104}$IL-2 was likely through the cysteine residue at position 125.

The entire $cys_3ala_{104}$IL-2 reaction mixture with the PEG reagent was then purified by RP-HPLC on a Vydac C4 column (0.46×25 cm) in an acetonitrile/TFA mobile phase. The IL-2 was loaded in 30% (w/v) acetonitrile, 0.1% (w/v) TFA and then eluted with a 45-min, 30–60% acetonitrile gradient in 0.1%

(w/v) TFA. Fractions were analyzed for IL-2 bioactivity and by reducing and non-reducing SDS-PAGE. The modified and unmodified IL-2 eluted together as a double peak, while the IL-2-IL-2 dimer eluted later in the chromatogram as a single peak (the IL-2 species eluting in the peaks were identified by SDS-PAGE analysis). All three species were active in the IL-2 bioassay; the modified and unmodified monomeric IL-2 had essentially equivalent activity, while the IL-2-IL-2 dimer had approximately 25% of the activity of the unmodified IL-2 (as determined by comparing the absorbance profile detected at 214 nm with the bioactivity profile).

Size-exclusion chromatography (SEC)-HPLC purification was found to be a useful method of separating PEG-IL-2 from unmodified IL-2. However, the presence of the cysteine residue at position 3 allows for dimer formation and these dimers were found to co-elute with PEGylated IL-2 during the SEC-HPLC purification step. Thus, an additional step, RP-HPLC, is required to further purify the PEG-IL-2 from the IL-2 dimers and yield a preparation free of oligomers. The IL-2 mutein was found to be covalently bound to PEG and to retain useful biological activity, but it was not shown conclusively that the attachment of the PEG is exclusively through the cysteine residue at position 3.

This purification process may be modified by changes in the media or process that would allow for the recovery of the IL-2 mutein in the absence of detergents such as SDS. In addition, a higher yield might be obtained by 1) harvesting and concentrating the yeast culture supernatant and performing a sizing step to reduce significantly the total amount of protein, and then 2) reacting the PEG reagent with the IL-2 mutein before the IL-2 has an opportunity to react with other cysteine residues from other proteins, and/or finishing the purification. In addition, the PEG reaction can be optimized by varying pH and ratios of reagents analogous to the previous example using the IL-2 mutein from *E. coli.*

Deposits

The following cultures were deposited in the Cetus Master Culture Collection (CMCC), 1400 Fifty-Third Street, Emeryville, Calif. 94608, USA and with the American Type Culture Collection (ATCC), 12301 Parklawn Drive, Rockville, Md. 20852-1776, USA, with the following CMCC/ATCC accession numbers and deposit dates:

| Vector Designation | CMCC Accession No. | CMCC Deposit Date | ATCC Deposit Date | ATCC Accession No. |
|---|---|---|---|---|
| pC3IL-2 | 3178 | 7/17/87 | 7/23/87 | 67,472 |
| pPM44 | 2589 | 12/10/85 | 12/13/85 | 53,357 |

The deposits above were made pursuant to a contract between the ATCC and the assignee of this patent application, Cetus Corporation. The contract with ATCC provides for permanent availability of the progeny of these cultures to the public on the issuance of the U.S. patent describing and identifying the deposits or the publications or upon the laying open to the public of any U.S. or foreign patent application, whichever comes first, and for availability of the progeny of these cultures to one determined by the U.S. Commissioner of Patents and Trademarks to be entitled thereto according to 35 USC §122 and the Commissioner's rules pursuant thereto (including 37 CFR §1.14) with particular reference to 886 OG 638). The assignee of the present application has agreed that if the cultures on deposit should die or be lost or destroyed when cultivated under suitable conditions, they will be promptly replaced on notification with a viable culture of the same culture.

In summary, the present invention is seen to provide an IL-2 mutein and a conjugate of the mutein or other IL-2 species to a PEG homopolymer or a polyoxyethylated polyol through one or more cysteine residues of the IL-2.

The foregoing written specification is considered to be sufficient to enable one skilled in the art to practice the invention. The present invention is not limited in scope by the culture deposited, since the deposited embodiment is intended as a single illustration of one aspect of the invention and any cultures that are functionally equivalent are within the scope of this invention. The deposit of material herein does not constitute an admission that the written description herein contained is inadequate to enable the practice of any aspect of the invention, including the best mode thereof, nor is the deposit to be construed as limiting the scope of the claims to the specific illustrations that it represents. Indeed, various modifications of the above-described modes for carrying out the invention that are obvious to those skilled in the field of molecular biology, protein chemistry, and pharmaceutical formulation or related fields are intended to be within the scope of the following claims.

What is claimed is:

1. An interleukin-2 mutein conjugate comprising a polymer covalently conjugated to an IL-2 mutein through a cystein residue, that is not essential to bioactivity, which has been introduced between amino acid positions 1 and 20 as measured from the N-terminus of the mature IL-2 sequence, wherein the polymer is selected from the group consisting of polyethylene glycol or polyoxyethylated polyols.

2. A conjugate in accordance with claim 1 wherein a cysteine is substituted for another amino acid, and this substitution does not affect bioactivity.

3. A conjugate of claim 1 wherein said polymer has an average molecular weight of 300 to 100,000 daltons.

4. A conjugate of claim 1 wherein said polymer has an average molecular weight of 4,000 to 40,000 daltons.

5. The conjugate of claim 1 wherein said polymer is conjugated to the IL-2 via reaction with 4-hydroxy-3-nitrobenzene sulfonate ester or the N-hydroxysuccinimde ester of a carboxylic acid of said polymer.

6. The conjugate of claim 1 wherein said polymer is conjugated to the IL-2 via reaction with a maleimido group.

7. The conjugate of claim 1 wherein said polymer is an unsubstituted polyethylene glycol homopolymer, a monomethyl polyethylene glycol homopolymer, or a polyoxyethylated glycerol.

8. The conjugate of claim 1 wherein said polymer is a monomethyl polyethylene glycol homopolymer.

9. The conjugate of claim 1 wherein said IL-2 is selectively conjugated via one cysteine residue.

10. The conjugate of claim 1 wherein said IL-2 has the native IL-2 amino acid sequence or is a mutein selected from the group consisting of $cys_3$IL-2, $cys_3ser_{125}$IL-2, $cys_3ala_{104}$IL-2, $cys_3ala_{104}ser_{125}$IL-2, des-$ala_1$-$cys_3$IL-2, des-$ala_1cys_3ser_{125}$IL-2, des-$ala_1cys_3ala_{104}$IL-2, des-$ala_1cys_3ala_{104}ser_{125}$IL-2, $cys_3ala_{125}$IL-2, cys- $_3ala_{104}ala_{125}$IL-2, des-$ala_1cys_3ala_{125}$IL-2, and des-$ala_1$-$cys_3ala_{104}ala_{125}$IL-2.

11. The conjugate of claim 1 wherein said IL-2 has the native IL-2 amino acid sequence or is the mutein, des-$ala_1cys_3ser_{125}$IL-2.

12. The pharmaceutical conjugate comprising the composition of claim 1 dissolved in a non-toxic, inert, pharmaceutically acceptable aqueous carrier medium.

* * * * *